(12) United States Patent
Chiba et al.

(10) Patent No.: US 8,252,543 B2
(45) Date of Patent: Aug. 28, 2012

(54) METHOD FOR DETECTING CANDIDATE ALZHEIMER'S DISEASE DRUG

(75) Inventors: Tomohiro Chiba, Tokyo (JP); Marina Yamada, Tokyo (JP); Kenzo Terashita, Tokyo (JP); Sadakazu Aiso, Tokyo (JP); Masaaki Matsuoka, Tokyo (JP)

(73) Assignees: Tomohiro Chiba, Tokyo (JP); Marina Yamada, Tokyo (JP); Kenzo Terashita, Tokyo (JP); Tomo Nishimoto, Ichikawa-shi (JP); Sadakazu Aiso, Tokyo (JP); Masaaki Matsuoka, Tokyo (JP)

( * ) Notice: Subject to any disclaimer, the term of this patent is extended or adjusted under 35 U.S.C. 154(b) by 149 days.

(21) Appl. No.: 11/896,494

(22) Filed: Aug. 31, 2007

(65) Prior Publication Data

US 2008/0102055 A1 May 1, 2008

(30) Foreign Application Priority Data

Oct. 12, 2006 (JP) ................................. 2006-279113

(51) Int. Cl.
*G01N 33/567* (2006.01)
*G01N 1/30* (2006.01)

(52) U.S. Cl. ..... 435/7.21; 435/7.95; 435/39; 435/40.52; 514/7.5

(58) Field of Classification Search ........................ None
See application file for complete search history.

(56) References Cited

FOREIGN PATENT DOCUMENTS

| | | | |
|---|---|---|---|
| EP | 1 754 485 A1 | 2/2007 | |
| JP | 2005-538683 A | 12/2005 | |
| JP | 2006-512419 A | 4/2006 | |
| JP | 2006-521115 A | 9/2006 | |
| WO | WO 03/051302 A2 | 6/2003 | |
| WO | WO 2004/058287 A2 | 7/2004 | |
| WO | WO 2004/084711 A2 | 10/2004 | |
| WO | WO 2005/097156 A1 | 10/2005 | |
| WO | WO 2006/004194 A1 | 1/2006 | |
| WO | WO 2007030693 | * | 3/2007 |

OTHER PUBLICATIONS

Rohn et al., Journal of Neuroscience, 28(12):3051-3059, Mar. 19, 2008.*
Dominguez-del-Toro et al., European Journal of Neuroscience, 20: 1945-1952, 2004.*
Bartoli et al., J Biol Chem, 275(43): 33189-33192, 2000.*
Hashimoto et al., Life Sci., 77(24):3092-3104, epublished Jul. 6, 2005.*
Chiba et al. J Neuroscience, 25(44): 10252-10261, Nov. 2, 2005.*
Doolittle et al., J Neurooncol., 81:81-91, 2007.*
Rosen et al., J Comp neurol, 509(3):259-270, Jul. 20, 2008.*
Konishi et al., Am J Physiol., 161(5), 1567-1576, 2002.*
Letter from Tom Hutcheon of the Society of Neuroscience regarding the 2006 Online Neuroscience Meeting Planner and 4 pages of attachments (Oct. 25, 2006).
Office Action issued Nov. 22, 2011, in Japanese Patent Application No. 2006-279113.

* cited by examiner

*Primary Examiner* — Daniel E Kolker
*Assistant Examiner* — Stacey MacFarlane
(74) *Attorney, Agent, or Firm* — Birch, Stewart, Kolasch & Birch, LLP

(57) ABSTRACT

The present invention provides a method for detecting or diagnosing in vitro Alzheimer's disease, or memory and/or cognitive disorders, using a human biological sample and the inactivation of STAT3 protein as an indication, and a method for screening for a therapeutic drug for Alzheimer's disease or memory and/or cognitive disorders, using the activation of STAT3 protein as an indication.

10 Claims, 5 Drawing Sheets
(4 of 5 Drawing Sheet(s) Filed in Color)

SEQUENCE LISTING

```
<160> NUMBER OF SEQ ID NOS: 4

<210> SEQ ID NO 1
<211> LENGTH: 770
<212> TYPE: PRT
<213> ORGANISM: Homo sapiens

<400> SEQUENCE: 1

Met Ala Gln Trp Asn Gln Leu Gln Gln Leu Asp Thr Arg Tyr Leu Glu
1               5                   10                  15

Gln Leu His Gln Leu Tyr Ser Asp Ser Phe Pro Met Glu Leu Arg Gln
            20                  25                  30

Phe Leu Ala Pro Trp Ile Glu Ser Gln Asp Trp Ala Tyr Ala Ala Ser
        35                  40                  45

Lys Glu Ser His Ala Thr Leu Val Phe His Asn Leu Leu Gly Glu Ile
    50                  55                  60

Asp Gln Gln Tyr Ser Arg Phe Leu Gln Glu Ser Asn Val Leu Tyr Gln
65                  70                  75                  80

His Asn Leu Arg Arg Ile Lys Gln Phe Leu Gln Ser Arg Tyr Leu Glu
                85                  90                  95

Lys Pro Met Glu Ile Ala Arg Ile Val Ala Arg Cys Leu Trp Glu Glu
            100                 105                 110

Ser Arg Leu Leu Gln Thr Ala Ala Thr Ala Ala Gln Gln Gly Gly Gln
        115                 120                 125

Ala Asn His Pro Thr Ala Ala Val Val Thr Glu Lys Gln Gln Met Leu
    130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
        195                 200                 205

Ala Leu Asp Gln Met Arg Arg Ser Ile Val Ser Glu Leu Ala Gly Leu
```

-continued

```
              210                 215                 220
Leu Ser Ala Met Glu Tyr Val Gln Lys Thr Leu Thr Asp Glu Leu
225                 230                 235                 240

Ala Asp Trp Lys Arg Arg Gln Gln Ile Ala Cys Ile Gly Gly Pro Pro
                245                 250                 255

Asn Ile Cys Leu Asp Arg Leu Glu Asn Trp Ile Thr Ser Leu Ala Glu
                260                 265                 270

Ser Gln Leu Gln Thr Arg Gln Ile Lys Lys Leu Glu Glu Leu Gln
                275                 280                 285

Gln Lys Val Ser Tyr Lys Gly Asp Pro Ile Val Gln His Arg Pro Met
290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
                340                 345                 350

Val Lys Phe Pro Glu Leu Asn Tyr Gln Leu Lys Ile Lys Val Cys Ile
                355                 360                 365

Asp Lys Asp Ser Gly Asp Val Ala Ala Leu Arg Gly Ser Arg Lys Phe
                370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                405                 410                 415

Arg Cys Gly Asn Gly Gly Arg Ala Asn Cys Asp Ala Ser Leu Ile Val
                420                 425                 430

Thr Glu Glu Leu His Leu Ile Thr Phe Glu Thr Glu Val Tyr His Gln
                435                 440                 445

Gly Leu Lys Ile Asp Leu Glu Thr His Ser Leu Pro Val Val Val Ile
                450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
                500                 505                 510

Ser Ser Thr Thr Lys Arg Gly Leu Ser Ile Glu Gln Leu Thr Thr Leu
                515                 520                 525

Ala Glu Lys Leu Leu Gly Pro Gly Val Asn Tyr Ser Gly Cys Gln Ile
530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
                580                 585                 590

Arg Glu Arg Ala Ile Leu Ser Thr Lys Pro Pro Gly Thr Phe Leu Leu
                595                 600                 605

Arg Phe Ser Glu Ser Ser Lys Glu Gly Gly Val Thr Phe Thr Trp Val
                610                 615                 620

Glu Lys Asp Ile Ser Gly Lys Thr Gln Ile Gln Ser Val Glu Pro Tyr
625                 630                 635                 640
```

```
Thr Lys Gln Gln Leu Asn Asn Met Ser Phe Ala Glu Ile Ile Met Gly
                645                 650                 655
Tyr Lys Ile Met Asp Ala Thr Asn Ile Leu Val Ser Pro Leu Val Tyr
            660                 665                 670
Leu Tyr Pro Asp Ile Pro Lys Glu Glu Ala Phe Gly Lys Tyr Cys Arg
        675                 680                 685
Pro Glu Ser Gln Glu His Pro Glu Ala Asp Pro Gly Ser Ala Ala Pro
    690                 695                 700
Tyr Leu Lys Thr Lys Phe Ile Cys Val Thr Pro Thr Thr Cys Ser Asn
705                 710                 715                 720
Thr Ile Asp Leu Pro Met Ser Pro Arg Thr Leu Asp Ser Leu Met Gln
                725                 730                 735
Phe Gly Asn Asn Gly Glu Gly Ala Glu Pro Ser Ala Gly Gly Gln Phe
            740                 745                 750
Glu Ser Leu Thr Phe Asp Met Glu Leu Thr Ser Glu Cys Ala Thr Ser
        755                 760                 765
Pro Met
    770

<210> SEQ ID NO 2
<211> LENGTH: 770
<212> TYPE: PRT
<213> ORGANISM: Mus musculus

<400> SEQUENCE: 2

Met Ala Gln Trp Asn Gln Leu Gln Gln Leu Asp Thr Arg Tyr Leu Glu
1               5                   10                  15
Gln Leu His Gln Leu Tyr Ser Asp Ser Phe Pro Met Glu Leu Arg Gln
                20                  25                  30
Phe Leu Ala Pro Trp Ile Glu Ser Gln Asp Trp Ala Tyr Ala Ala Ser
            35                  40                  45
Lys Glu Ser His Ala Thr Leu Val Phe His Asn Leu Leu Gly Glu Ile
        50                  55                  60
Asp Gln Gln Tyr Ser Arg Phe Leu Gln Glu Ser Asn Val Leu Tyr Gln
65                  70                  75                  80
His Asn Leu Arg Arg Ile Lys Gln Phe Leu Gln Ser Arg Tyr Leu Glu
                85                  90                  95
Lys Pro Met Glu Ile Ala Arg Ile Val Ala Arg Cys Leu Trp Glu Glu
                100                 105                 110
Ser Arg Leu Leu Gln Thr Ala Thr Ala Ala Gln Gln Gly Gly Gln
            115                 120                 125
Ala Asn His Pro Thr Ala Ala Val Val Thr Glu Lys Gln Gln Met Leu
    130                 135                 140
Glu Gln His Leu Gln Asp Val Arg Lys Arg Val Gln Asp Leu Glu Gln
145                 150                 155                 160
Lys Met Lys Val Val Glu Asn Leu Gln Asp Asp Phe Asp Phe Asn Tyr
                165                 170                 175
Lys Thr Leu Lys Ser Gln Gly Asp Met Gln Asp Leu Asn Gly Asn Asn
            180                 185                 190
Gln Ser Val Thr Arg Gln Lys Met Gln Gln Leu Glu Gln Met Leu Thr
        195                 200                 205
Ala Leu Asp Gln Met Arg Arg Ser Ile Val Ser Glu Leu Ala Gly Leu
    210                 215                 220
Leu Ser Ala Met Glu Tyr Val Gln Lys Thr Leu Thr Asp Glu Glu Leu
225                 230                 235                 240
```

```
Ala Asp Trp Lys Arg Arg Gln Gln Ile Ala Cys Ile Gly Gly Pro Pro
            245                 250                 255

Asn Ile Cys Leu Asp Arg Leu Glu Asn Trp Ile Thr Ser Leu Ala Glu
            260                 265                 270

Ser Gln Leu Gln Thr Arg Gln Ile Lys Lys Leu Glu Glu Leu Gln
    275                 280                 285

Gln Lys Val Ser Tyr Lys Gly Asp Pro Ile Val Gln His Arg Pro Met
    290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
            340                 345                 350

Val Lys Phe Pro Glu Leu Asn Tyr Gln Leu Lys Ile Lys Val Cys Ile
            355                 360                 365

Asp Lys Asp Ser Gly Asp Val Ala Ala Leu Arg Gly Ser Arg Lys Phe
        370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                405                 410                 415

Arg Cys Gly Asn Gly Gly Arg Ala Asn Cys Asp Ala Ser Leu Ile Val
                420                 425                 430

Thr Glu Glu Leu His Leu Ile Thr Phe Glu Thr Glu Val Tyr His Gln
        435                 440                 445

Gly Leu Lys Ile Asp Leu Glu Thr His Ser Leu Pro Val Val Val Ile
    450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
            500                 505                 510

Ser Ser Thr Thr Lys Arg Gly Leu Ser Ile Glu Gln Leu Thr Thr Leu
            515                 520                 525

Ala Glu Lys Leu Leu Gly Pro Gly Val Asn Tyr Ser Gly Cys Gln Ile
    530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
                580                 585                 590

Arg Glu Arg Ala Ile Leu Ser Thr Lys Pro Pro Gly Thr Phe Leu Leu
        595                 600                 605

Arg Phe Ser Glu Ser Ser Lys Glu Gly Gly Val Thr Phe Thr Trp Val
    610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
                645                 650                 655

Tyr Lys Ile Met Asp Ala Thr Asn Ile Leu Val Ser Pro Leu Val Tyr
                660                 665                 670
```

```
Leu Tyr Pro Asp Ile Pro Lys Glu Glu Ala Phe Gly Lys Tyr Cys Arg
            675                 680                 685

Pro Glu Ser Gln Glu His Pro Glu Ala Asp Pro Gly Ser Ala Ala Pro
    690                 695                 700

Tyr Leu Lys Thr Lys Phe Ile Cys Val Thr Pro Thr Thr Cys Ser Asn
705                 710                 715                 720

Thr Ile Asp Leu Pro Met Ser Pro Arg Thr Leu Asp Ser Leu Met Gln
                725                 730                 735

Phe Gly Asn Asn Gly Glu Gly Ala Gly Pro Ser Ala Gly Gly Gln Phe
            740                 745                 750

Glu Ser Leu Thr Phe Asp Met Asp Leu Thr Ser Glu Cys Ala Thr Ser
        755                 760                 765

Pro Met
    770

<210> SEQ ID NO 3
<211> LENGTH: 26
<212> TYPE: PRT
<213> ORGANISM: Artificial
<220> FEATURE:
<223> OTHER INFORMATION: Synthetic peptide

<400> SEQUENCE: 3

Ser Ala Leu Leu Arg Ser Ile Pro Ala Pro Ala Gly Ala Ser Arg Leu
1               5                   10                  15

Leu Leu Leu Thr Gly Glu Ile Asp Leu Pro
            20                  25

<210> SEQ ID NO 4
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MUTAGEN
<222> LOCATION: (11)..(11)
<223> OTHER INFORMATION: Xaa at position 11 is Arg or Ala and is part of
      the tetrapeptide Xn1 (residues 11-14)
<220> FEATURE:
<221> NAME/KEY: MUTAGEN
<222> LOCATION: (12)..(12)
<223> OTHER INFORMATION: Xaa at position 12 is Gly or Ala and is part of
      the tetrapeptide Xn1 (residues 11-14)
<220> FEATURE:
<221> NAME/KEY: MUTAGEN
<222> LOCATION: (13)..(13)
<223> OTHER INFORMATION: Xaa at position 13 is Phe or Ala and is part of
      the tetrapeptide Xn1 (residues 11-14)
<220> FEATURE:
<221> NAME/KEY: MUTAGEN
<222> LOCATION: (14)..(14)
<223> OTHER INFORMATION: Xaa at position 14 is Ser or Ala and is part of
      the tetrapeptide Xn1 (residues 11-14)
<220> FEATURE:
<221> NAME/KEY: MUTAGEN
<222> LOCATION: (15)..(15)
<223> OTHER INFORMATION: Xaa represents Cys, Arg, Lys or His
<220> FEATURE:
<221> NAME/KEY: MUTAGEN
<222> LOCATION: (16)..(16)
<223> OTHER INFORMATION: Xaa represents Leu or Arg
<220> FEATURE:
<221> NAME/KEY: MUTAGEN
<222> LOCATION: (17)..(17)
<223> OTHER INFORMATION: Xaa at position 17 is Leu or Ala and is part of
      the dipeptide Xn2 (residues 17-18)
<220> FEATURE:
<221> NAME/KEY: MUTAGEN
```

-continued

```
<222> LOCATION: (18)..(18)
<223> OTHER INFORMATION: Xaa at position 18 is Leu or Ala and is part of
      the dipeptide Xn2 (residues 17-18)
<220> FEATURE:
<221> NAME/KEY: MUTAGEN
<222> LOCATION: (21)..(21)
<223> OTHER INFORMATION: Xaa represents Gly, L-Ser or D-Ser
<220> FEATURE:
<221> NAME/KEY: MUTAGEN
<222> LOCATION: (22)..(22)
<223> OTHER INFORMATION: Xaa at position 22 is Glu or Ala and is part of
      the tetrapeptide Xn3 (residues 22-25)
<220> FEATURE:
<221> NAME/KEY: MUTAGEN
<222> LOCATION: (23)..(23)
<223> OTHER INFORMATION: Xaa at position 23 is Ile or Ala and is part of
      the tetrapeptide Xn3 (residues 22-25)
<220> FEATURE:
<221> NAME/KEY: MUTAGEN
<222> LOCATION: (24)..(24)
<223> OTHER INFORMATION: Xaa at position 24 is Asp or Ala and is part of
      the tetrapeptide Xn3 (residues 22-25)
<220> FEATURE:
<221> NAME/KEY: MUTAGEN
<222> LOCATION: (25)..(25)
<223> OTHER INFORMATION: Xaa at position 25 is Leu or Ala and is part of
      the tetrapeptide Xn3 (residues 22-25)

<400> SEQUENCE: 4

Ser Ala Leu Leu Arg Ser Ile Pro Ala Pro Xaa Xaa Xaa Xaa Xaa Xaa
1               5                   10                  15

Xaa Xaa Leu Thr Xaa Xaa Xaa Xaa Xaa Pro
            20                  25
```

METHOD FOR DETECTING CANDIDATE ALZHEIMER'S DISEASE DRUG

BACKGROUND OF THE INVENTION

1. Field of the Invention

The present invention relates to a new method for detecting Alzheimer's disease. Specifically, the present invention relates to a method for detecting or diagnosing Alzheimer's disease using the inactivation of STAT3 protein as an indication.

The present invention also relates to a method for screening for an agent for treating Alzheimer's disease, using the activation of STAT3 protein as an indication.

The present invention further relates to a pharmaceutical composition for treating Alzheimer's disease, comprising a drug that activates the STAT3 protein.

2. Background of the Invention

Alzheimer's disease (AD) is the most common neurodegenerative disease, which is characterized clinically by progressive memory loss and cognitive dysfunction and pathologically by senile plaques, neurofibrillary tangles, and neuron death (Mattson M P (2004) Nature 430: 631-639).

In the previous studies, we have prepared Colivelin by attaching activity-dependent neurotrophic factor (ADNF) to a potent Human (HM) derivative (Chiba T, Yamada M, Hashimoto Y, Sato M, Sasabe J, Kita Y, Terashita K, Aiso S, Nishimoto I, Matsuoka M (2005) J Neurosci 25: 10252-10261). HN is a neuroprotection factor isolated and identified from an occipital lobe of an Alzheimer's disease patient and has antagonistic effects on various types of Alzheimer's disease-relevant neurotoxicity (Hashimoto Y, Niikura T, Tajima H, Yasukawa T, Sudo H, Ito Y, Kita Y, Kawasumi M, Kouyama K, Doyu M, Sobue G, Koide T, Tsuji S, Lang J, Kurokawa K, Nishimoto I (2001) Proc Natl Acad Sci U.S.A. 98: 6336-6341). Furthermore, we have demonstrated that HN-mediated neuroprotection takes place via the activation of STAT3 molecule in vitro (Chiba T et al., (2005) above; Hashimoto Y, Suzuki H, Aiso S, Niikura T, Nishimoto I, Matsuoka M (2005) Life Sci 77: 3092-3104).

STAT (signal transducer and activator of transcription) is a protein molecule that broadly exists in multicellular organisms and plays roles in a variety of cellular events, such as development, cell proliferation, and cell death (Stephanou A, Latchman D S (2005) Growth Factors 23(3): 177-82). Seven different STAT family members have been identified to date: STAT1, STAT2, STAT3, STAT4, STAT5α, STAT5β, and STAT6. These molecules are thought to be important molecules of cytokine receptor-mediated signaling. Of these, STAT3 seems to be responsible for particularly important functions in vivo because STAT3 knockout mice showed a phenotype of embryonic lethality at the early stage of development (Takeda K, Noguchi K, Shi W, Tanaka T, Matsumoto M, Yoshida N, Kishimoto T, Akira S (1997) Proc Natl Acad Sci U.S.A. 15; 94(8): 38014). In addition, it has been reported that STAT-3 bears a function to restrict apoptosis in various types of cells (Chen R H, Chang M C, Su Y H, Tsai Y T, Kuo M L (1999) J Biol Chem. 274(33): 23013-9; Grandis J R, Drenning S D, Zeng Q, Watkins S C, Melhem M F, Endo S, Johnson D E, Huang L, He Y, Kim J D (2000) Proc Natl Acad Sci U.S.A. 97(8): 4227-32).

We have now examined the pathological relationship between Alzheimer's disease and STAT3 protein (i.e., the pathological contribution of STAT3), using brain tissues of Alzheimer's disease animal models and Alzheimer's disease patients. STAT3 is a molecule having important cellular functions including an anti-apoptotic function (i.e., cell survival) in various types of cells. However, the relationship of STAT3 with the pathological conditions of Alzheimer's disease has remained unknown.

SUMMARY OF THE INVENTION

The present invention includes the following characteristics.

According to the first aspect, the present invention provides a method for detecting or diagnosing Alzheimer's disease, or memory and/or cognitive disorders, comprising detecting or diagnosing in vitro Alzheimer's disease, or memory and/or cognitive disorders, using a human biological sample and the inactivation of STAT3 protein as an indication.

According to the second aspect, the present invention provides a method for screening for a therapeutic agent for human Alzheimer's disease or memory and/or cognitive disorders, comprising screening for a therapeutic agent for human Alzheimer's disease or memory and/or cognitive disorders, using a non-human Alzheimer's disease animal model, or a brain-derived primary neuronal cultured cell or a nervous system cell like cultured cell line, which cell or cell line is derived from an animal with Alzheimer's disease, and a candidate drug, and using the activation of STAT3 protein as an indication.

According to the third aspect, the present invention provides a pharmaceutical composition for treating or preventing Alzheimer's disease or memory and/or cognitive disorders, comprising a drug that activates STAT3 protein, as an active ingredient.

According to the present invention, there is provided a new method for detecting Alzheimer's disease or memory and/or cognitive disorders. We have now discovered that these diseases pathologically relate to STAT3 inactivation and that the activation of STAT3 ameliorates cognitive functions and memory. This makes it possible to screen for a therapeutic agent using the activation of STAT3 as an indication. Therefore, the present invention is to provide a surprising effect in treating and detecting or diagnosing Alzheimer's disease or memory and/or cognitive disorders.

BRIEF DESCRIPTION OF THE DRAWINGS

The patent or application file contains at least one drawing executed in color. Copies of this patent or patent application publication with color drawing(s) will be provided by the office upon request and payment of the necessary fee.

FIG. 1 shows the results of phosphorylated STAT3 (which may be referred to as "phospho-STAT3" hereinafter) staining performed before the onset (at 6-month-old) and after the onset (at 28-month-old) of Alzheimer's disease in V642I-APP knockin mice. FIGS. 1A and 1B are hippocampus images of wild-type littermates (control mice), and FIGS. 1C and 1D are the same of knockin mice. At 6 months of age (FIGS. 1A and 1C), no differences were observed between the two groups. However, at 28 months of age (FIGS. 1B and 1D), the level of phospho-STAT3 staining (brown) was significantly decreased in knockin mice, compared with wild-type control mice. When wild-type mice alone were observed (FIGS. 1A and 1B), the staining was decreased in 28-month-old mice compared with 6-month-old mice. This suggests that STAT3 is inactivated in the age-dependent manner. The phospho-STAT3 staining at early stage (3-month-old), middle stage (12-month-old), or late stage (18-month-old) of Tg2576 mice is also shown. FIGS. 1E to 1G depict the staining in wild-type control littermates and FIGS. 1H to 1J depict the staining in Tg2576 mice. In case of Tg2576 mice, the decrease in phospho-STAT3 staining was observed at all stages.

FIGS. 5A and 5B denote wild-type mice to which a vehicle had been administered; FIGS. 5C and 5D denote wild-type mice to which Colivelin had been administered; FIGS. 5E and 5F denote Tg2576 to which the vehicle had been administered; and FIGS. 5G and 5H denote the hippocampus of Tg2576 to which Colivelin had been administered. In the case of wild-type mice, STAT3 phosphorylation (brown) levels in the hippocampus were slightly increased by Colivelin administration. Compared with the wild-type mice to which the vehicle had been administered, significant decreases were observed in phosphorylated STAT3 levels in the case of Tg2576 to which the vehicle had been administered. As a result of Colivelin administration, STAT3 phosphorylation was also observed in Tg2576 hippocampus at levels close to those in the case of wild-type mice to which the vehicle had been administered.

DESCRIPTION OF THE PREFERRED EMBODIMENTS

Figure 1:
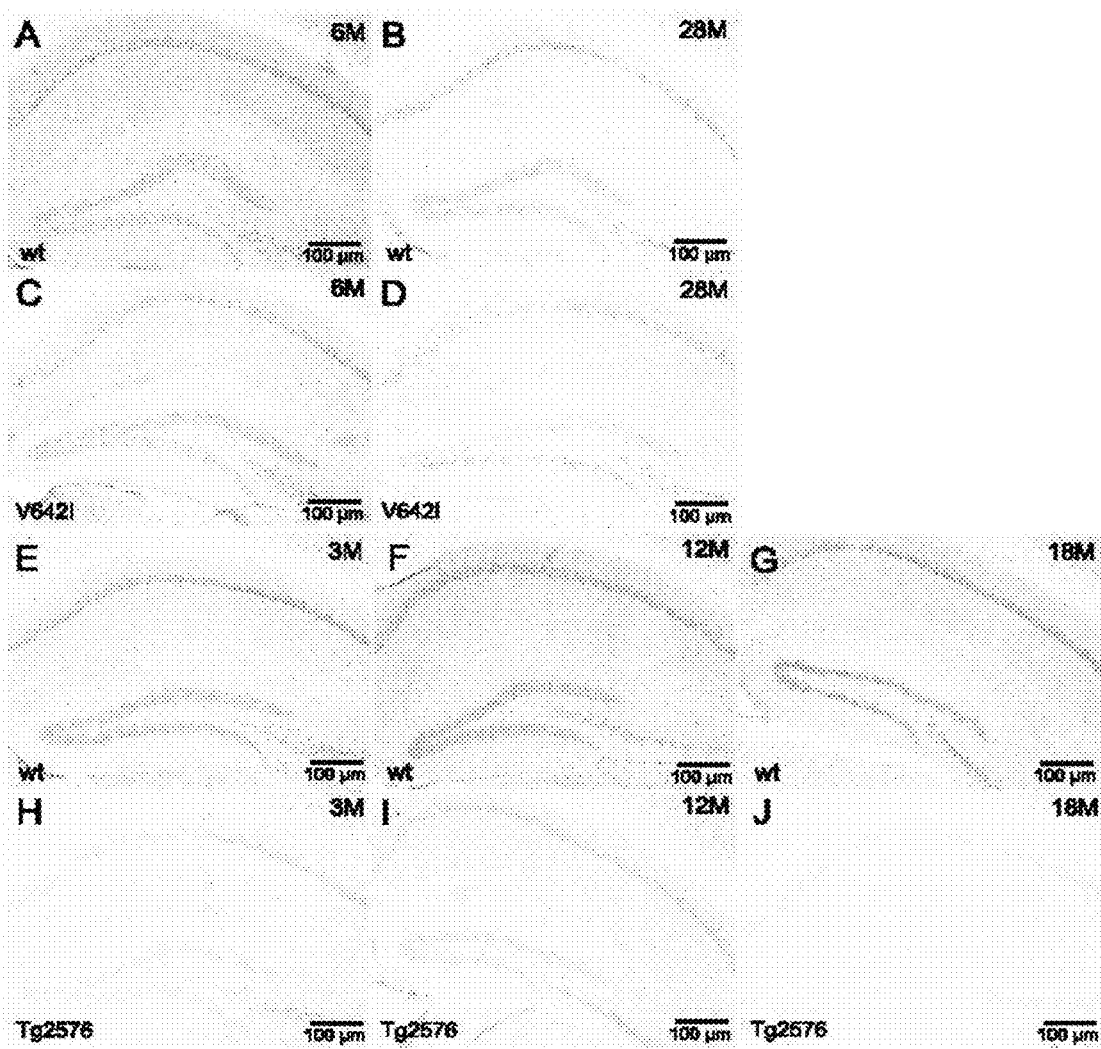
FIG. 1 shows age-dependent STAT3 inactivation in Alzheimer's disease model mice. Specifically.
Figure 2:
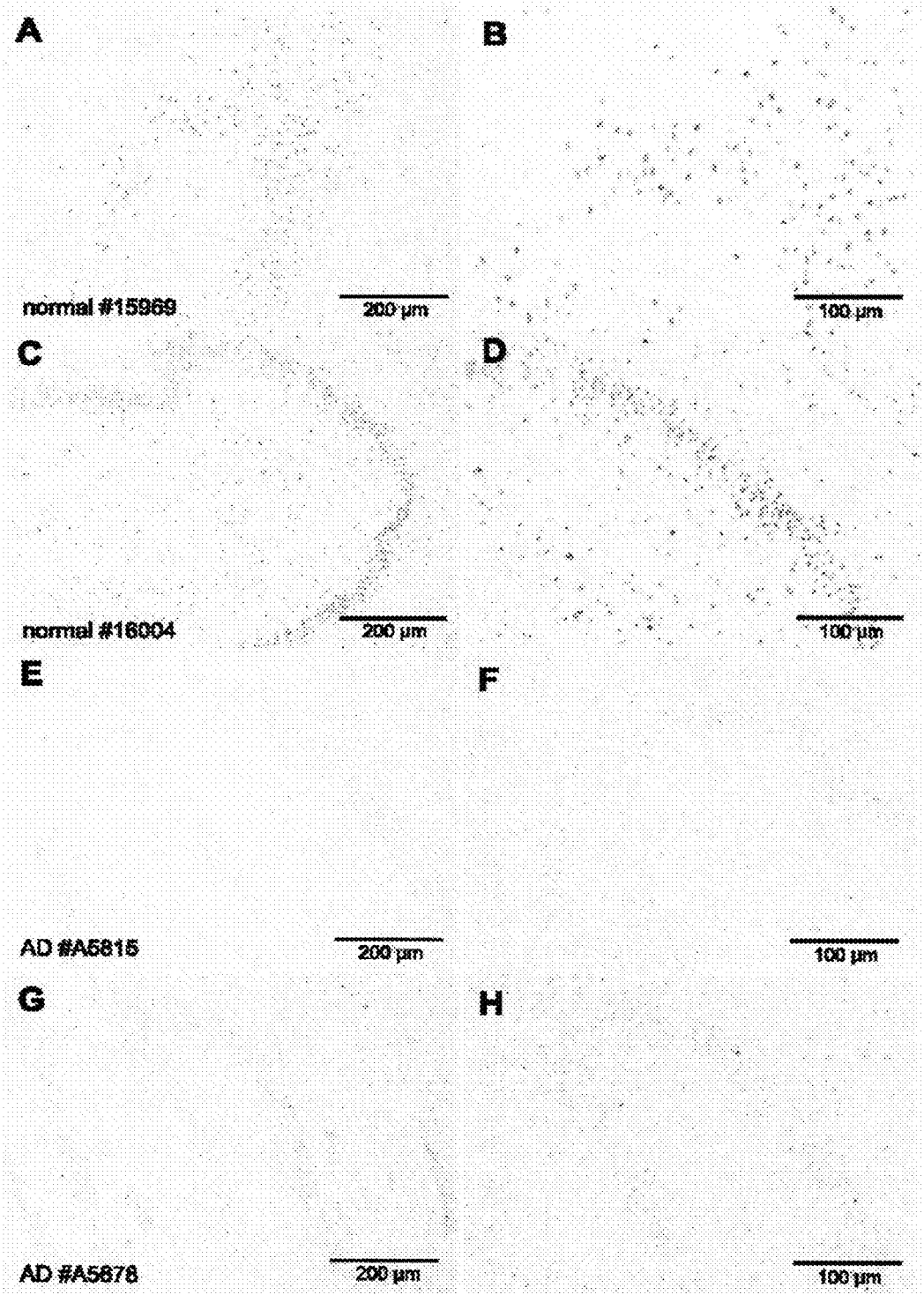
FIG. 2 shows STAT3 inactivation in the hippocampus of Alzheimer's disease patients. The hippocampal sections from patients with clinically and histopathologically diagnosed Alzheimer's disease (E-H, AD #A5815 and #A5678, Kawasaki Hospital, Kanagawa, Japan) and age-matched hippocampal sections from healthy brains (FIGS. 2A-2D, #15969 and #16004, Keio University Hospital, Tokyo, Japan) were stained with an anti-phospho-STAT3 antibody. Strong phospho-STAT3 staining images were observed for the hippocampus of the healthy brains, whereas almost no staining by the anti-phospho-STAT3 antibody was observed for the Alzheimer's disease brains.

The present invention will be described in more detail.

1. Method for Detecting Alzheimer's Disease or Memory and/or Cognitive Disorders The present invention provides a method for detecting or diagnosing Alzheimer's disease or memory and/or cognitive disorders, comprising detecting in vitro Alzheimer's disease or memory and/or cognitive disorders with the use of a human biological sample and STAT3 protein inactivation as an indication, as described above.

β-amyloid (Aβ) that is a major component of senile plaques has been thought to be an important target molecule for development of a therapeutic drug for Alzheimer's disease. Recently, it has been reported that even among 30% of healthy elderly subjects for which no abnormality has been observed in their cognitive functions, senile plaques and neurofibrillary tangles are present at such a level that they can be diagnosed with Alzheimer's disease (Bennett D A, Schneider J A, Arvanitakis Z, Kelly J F, Aggarwal N T, Shah R C, Wilson R S. (2006) Neurology 66(12): 1837-44). This report strongly suggests that possible presence of pathological changes more specific to Alzheimer's disease in addition to senile plaques and neurofibrillary tangles.

Based on the finding that the STAT3 protein controls cognitive functions, we have now further found that an STAT3 molecule is inactivated with aging in the hippocampus of Alzheimer's disease model mice and Alzheimer's disease patients. We have now further found that the activation of the STAT3 protein in Alzheimer's disease model mice using Colivelin (a Humanin derivative) led to the complete recovery of the cognitive functions of the mice. Based on these results, we concluded that pathologically significant relationship is present between STAT3 protein inactivation in the brain, particularly in the hippocampus, and Alzheimer's disease or memory and/or cognitive disorders. Moreover, it reveals that STAT3 protein activation is therapeutically effective for amelioration of Alzheimer's disease conditions, particularly the amelioration of memory and cognitive functions.

In the present invention, the "inactivation of STAT3 protein" indicates almost or complete loss of the biological functions of STAT3 protein, or significantly reduced or decreased functions of STAT3 protein when compared with those of a normal control. According to the embodiments of the present invention, such inactivation indicates reduced or decreased phosphorylation of STAT3 protein. In deed, as demonstrated by Examples described later, phosphorylated STAT3 levels were significantly decreased in the hippocampus regions of the brains of Alzheimer's disease patients. Therefore, measurement of a phosphorylated STAT3 level using a human biological sample makes it possible to detect or diagnose Alzheimer's disease or memory and/or cognitive disorders.

In an embodiment of the present invention, such a biological sample is a brain tissue. In particular, the hippocampus is a preferable brain tissue. However, no significant differences were observed in the cerebral cortex in terms of the STAT3 phosphorylation. Biological samples can be obtained from the brains of patients or deceased patients with unknown etiology (i.e., whether or not the cause is Alzheimer's disease is unknown). In the case of a diseased patient, a biological sample can be obtained from the patient in order to determine the cause of death.

The inactivation of STAT3 protein can be measured using a general immunological method. Examples of such immunological method include an immunohistological staining method, an immunoblot method, an enzyme linked immunosorbent assay (ELISA), and a flow cytometry method.

For an immunological method, an antibody specific to a phosphorylated STAT3 protein is generally used. Such specific antibody is preferably a monoclonal antibody and is an antibody that specifically recognizes a phosphorylated STAT3 protein.

A monoclonal antibody can be prepared by techniques as described in Köhler and Milstein (Nature 256: 495, 1975) or Tatsuo Iwasaki et al., (Monoclonal Antibody, Hybrid and ELISA, Kodansha Scientific, Tokyo, Japan, 1987), for example. Briefly, this technique involves the steps of: immunizing a mouse (e.g., via intraperitoneal injection) with phosphorylated STAT3, confirming antibody production, removing the spleen, and then preparing splenocytes from the spleen; preparing hybridomas by cell fusion of splenocytes and myeloma cells (e.g., X63 cell line and NS-1 cell line) at a ratio ranging from 1:1 to 10:1 in medium such as RPMI1640 containing polyethylene glycol (e.g., PEG1000 to 6000), for example; screening for antibody-producing hybridomas in HAT (hypoxanthine, aminopterin, and thymidine) medium from among hybridomas; intraperitoneally cloning the antibody-producing hybridoma in the abdomen of a mouse and collecting monoclonal antibodies from the ascite; screening for monoclonal antibodies that specifically react with the phosphorylated STAT3 protein, but does not react with the STAT3 protein; and the like.

According to histological immunoassay, a paraffin-embedded or a frozen section is prepared from a tissue sample, an antigen-antibody reaction is performed using a labeled phospho-STAT3 specific antibody prepared as described above, and then the thus obtained staining images can be observed microscopically or electron-microscopically. Such an antibody can be labeled with a fluorescent dye (e.g., FITC or TRITC), an enzyme (e.g., horseradish peroxidase or alkaline phosphatase), or the like. Alternatively, the detection can be performed using a secondary antibody similarly labeled with fluorescent dye or enzyme. Alternatively, a biotin/avidin or a streptavidin system can also be used.

In the method of the present invention, the STAT3 protein is a human-derived protein containing the amino acid sequence of SEQ ID NO: 1. However, mutants of the STAT3 protein generated due to polymorphism, alternative splicing, or the like are also subjects of the present invention. Such mutants have an amino acid sequence comprising a deletion, substitution, or addition of one or several amino acids in the amino acid sequence of SEQ ID NO: 1, or comprises an amino acid sequence having at least 90%, preferably at least 95%, more preferably at least 98% identity, to the amino acid sequence of SEQ ID NO: 1.

2. Therapeutic Agent and Method for Screening for the Same

The present invention further provides a method for screening for a therapeutic agent for human Alzheimer's disease or memory and/or cognitive disorders, which comprises screening for a therapeutic agent for human Alzheimer's disease or memory and/or cognitive disorders, using a non-human animal model for Alzheimer's disease, or a brain-derived primary neuronal cultured cell or a nervous system cell like cultured cell line, which cell or cell line is derived from an animal with Alzheimer's disease, and a candidate drug, and using the activation of STAT3 as an indication.

We have now found that, in Alzheimer's disease animal models, inactivated STAT3 (which indicates a significant decrease in phosphorylated STAT3 protein level) is phosphorylated and re-activated through administration of a drug capable of enhancing STAT3 phosphorylation, such as Colivelin having the following amino acid sequence, for example: Ser-Ala-Leu-Leu-Arg-Ser-Ile-Pro-Ala-Pro-Ala-Gly-Ala-Ser-Arg-Leu-Leu-Leu-Leu-Thr-Gly-Glu-Ile-Asp-Leu-Pro (SEQ ID NO: 3), so as to recover memory and cognitive functions at normal levels. The present invention is based on said findings, and therefore enables screening for a therapeutic agent for Alzheimer's disease or memory and/or cognitive disorders using the activation of STAT3 protein as an indication.

In the method of the present invention, the degree of the STAT3 protein activation may be quantitatively determined or visually determined. In both cases, it is desired to determine the degree of the STAT3 protein activation, particularly an increase in phosphorylation level when compared with that of a normal control.

In the screening method of the present invention, non-human Alzheimer's disease animal models, or brain-derived primary neuronal cultured cells, or nervous system cell like cultured cell lines, which cells or cell lines are derived from an animal with Alzheimer's disease (including human), can be used.

Examples of the nervous system cell like cultured cell lines include PC12 cells (Greene L A, Tischler A S. (1976) Proc Natl Acad Sci U.S.A. 73(7): 2424-2428), F11 cells (Mugnai (Lewandowska K, Culp L A. (1988) Eur J Cell Biol. 46(2): 352-361), NSC34 cells (Cashman N R, Durham H D, Blusztajn J K, Oda K, Tabira T, Shaw I T, Dahrouge S, Antel J P. (1992) Dev Dyn. 194(3): 209-221), and SHSY-5Y cells (Odelstad L, Pahlman S, Nilsson K, Larsson E, Lackgren Q Johansson K E, Hjerten S, Grotte G. (1981) Brain Res. 224 (1): 69-82).

In this case, the brain-derived primary neuronal cultured cells or nervous system cell like cultured cell lines are cultured in a medium supplemented with a candidate drug, and then the degree of the STAT3 protein phosphorylation can be immunologically measured using an anti-phospho-STAT3 antibody. The STAT3 protein is liberated from cells, reacted with a $^{125}$I-labeled antibody, for example, and then subjected to size separation by SDS-PAGE or the like. The resultant complex is then subjected to autoradiography, so that the degree of phosphorylation can be measured. The density of a band can be quantified on densitometer.

Examples of non-human animal models include rodents such as mice and rats. Specific examples of the same that can be used include an APP knockin (KI) mouse (referred to as "V642I-APP knockin mouse") having London type FAD mutation (V642I) of amyloid precursor protein (APP), which mouse has characteristics closest to those of human V6421 mutant FAD patients, and transgenic (Tg) mice (Tg2576) produced by introducing Swedish type mutation (another FAD causative gene) into mice and then causing overexpression of the gene (Hsiao K, Chapman P, Nilsen S, Eclanan C, Harigaya Y, Younkin S, Yang F, Cole G. (1996) Science 274 (5284): 99-102).

When screening is performed using a non-human animal model, a candidate drug is administered to the animal, a brain tissue, preferably a hippocampal section, is sampled from the animal, and then the degree of the STAT3 protein activation (or phosphorylation) can be measured using an immunohistological staining method such as an immunohistological staining method, an immunoblot method, an enzyme linked immuno-sorbent assay (ELISA), a flow cytometry method, or the like using a specific antibody. Administration can be performed via oral administration, parenteral administration (e.g., intravenous, intranasal, subcutaneous, intradermal, intraperitoneal, or intracerebral administration), or the like. However, the examples are not limited thereto. Upon immunohistological staining, a specific antibody against the phosphorylated STAT3 protein is used, as described above. At this time, the antibody bound to phosphorylated STAT3 protein can be detected by labeling it with an enzyme or a fluorescent dye or by using a labeled secondary antibody.

An example of a candidate drug to be used herein is a small organic molecule or a peptide, polypeptide, protein, or chemically modified derivative thereof.

Examples of such chemically modified derivative include sugar-binding derivatives, phosphorylated derivatives, sulfated derivatives, pegylated derivatives, acylated derivatives, and alkylated derivatives.

A preferable candidate drug is a substance that enhances STAT3 protein phosphorylation. An example of such substance is Colivelin, CNTF (ciliary neurotrophic factor), interleukin-6 (IL-6), or a derivative thereof (Stephanou A et al., Growth Factors (2005) 23(3): 177-82). Examples of such derivative include a pharmaceutically acceptable salt a mutant comprising a substitution, deletion, or addition of an amino acid(s) and retaining biological activity (preferably having 90% or more, 95% or more, or 98% or more sequence identity), a chemically modified derivative (e.g., a sugar-binding derivative, an acylated derivative, a phosphorylated derivative, and an alkylated derivative, preferably a modified derivative capable of passing through the blood-brain barrier).

A particularly preferable candidate drug is Colivelin or its derivative thereof. An example of such derivative is a peptide or polypeptide comprising a deletion, substitution, insertion, and/or addition of one or several amino acids in the amino acid sequence of SEQ ID NO: 3 of Colivelin and enhancing the phosphorylation of STAT3 protein. Alternatively, another example of such candidate drug is a peptide or a polypeptide which is represented by the following amino acid sequence (SEQ ID NO: 4):
Ser-Ala-Leu-Leu-Arg-Ser-Ile-Pro-Ala-Pro-$Xn_1$-(Cys or Arg or Lys or His)-(Leu or Arg)-$Xn_2$-Leu-Thr-(Gly or L-Ser or D-Ser)-$Xn_3$-Pro
[wherein $Xn_1$ has an amino acid sequence comprising (Arg or Ala)-(Gly or Ala)-(Phe or Ala)-(Ser or Ala), X2 has an amino acid sequence comprising (Leu or Ala)-(Leu or Ala), and $Xn_3$ has an amino acid sequence comprising (Glu or Ala)-(Ile or Ala)-(Asp or Ala)-(Leu or Ala)] and enhances the phosphorylation of STAT3 protein.

The dose of a candidate drug to be administered to an animal model is, but is not limited to, a dose ranging from 0.1 mg/kg body weight to 1 mg/kg body weight. Various doses may be tested to determine an effective dose.

In an embodiment of the present invention, the STAT3 protein differs depending on non-human animal models to be used herein or on the origins of cell lines to be used herein. For example, the STAT3 protein is derived from a human or a mouse and is a protein having the amino acid sequence of SEQ ID NO: 1 or 2, respectively. Furthermore, STAT3 protein mutants generated due to polymorphism, alternative splicing, or the like are also subjects of the present invention. Such mutants have an amino acid sequence comprising a deletion, substitution, or addition of one or several amino acids in the amino acid sequence of SEQ ID NO: 1 or 2 and retain STAT3 biological activity.

A drug that is found by the screening method of the present invention, i.e., a drug that activates (or phosphorylates) the STAT3 protein, can be used for treating or preventing Alzheimer's disease or memory and/or cognitive disorders.

Accordingly, the present invention also provides a pharmaceutical composition comprising such a drug as the active ingredient. A particularly effective drug is Colivelin or derivatives thereof as described above.

When the pharmaceutical composition of the present invention is administered via oral administration, the composition may be formulated into a dosage form such as tablets, capsules, fine granules, powders, pills, liquor for internal use, suspensions, solutions, emulsions, syrups, or sustained release formulations. The composition may also be formulated into a dry dosage form that can be reconstituted when used. Furthermore, when the pharmaceutical composition of the present invention is administered parenterally, the composition may be formulated into a dosage form, such as injections (e.g., intravenous injections (including drip), intramuscular injections, intraperitoneal injections, and subcutaneous injections) or suppositories. In the case of formulations for injection, the composition is provided in the form of a unit dosage ampule or a multiple dosage container. Furthermore, the composition may be formulated so that it can pass through the blood-brain barrier of a patient, or that it may also be formulated into a dosage form for intraspinal or intraventricular administration.

These various formulations can be prepared according to a standard method by adequately selecting pharmaceutically acceptable excipients, expanders, binders, wetting agents, disintegrators, lubricants, surfactants, dispersants, buffers, preservatives, solubilizers, antiseptics, taste and flavor corrigents, soothing agents, stabilizers, tonicity agents, and the like that are known or conventionally used in the pharmaceutical industry (Remington: The Science and Practice of Pharmacy, $19^{th}$ ed., Vol. I and Vol. II, 1995, Mack Publishing Company). Moreover, in the pharmaceutical composition, the content of a polypeptide of the present invention, which is an active ingredient, is, but is not limited to, an amount ranging from about 0.001 to about 10% by weight, for example. Alternatively, the concentration of such an active ingredient in the composition is, but is not limited to, about 100 fM or more, about 1 pM or more, about 1 nM or more, about 10 nM or more, about 100 nM or more, and about 1 μM or more, for example.

When the pharmaceutical composition of the present invention is used as an agent for preventing or treating Alzheimer's disease or memory and/or cognitive disorders, the agent can be administered parenterally or orally to a human. The dose or the frequency of administration of the agent of the present invention can be adequately varied depending on the ages, sexes, symptoms, and administration routes of subjects to be administered. For example, the effective dose of the polypeptide of the present invention, which is combined with an appropriate diluent or a pharmacologically usable carrier, ranges from about 1 μg to about 500 μg per kg body weight a day, but is not limited thereto.

The present invention will hereafter be described in more detail with reference to the following examples, although the technical scope of the present invention is not limited thereto.

EXAMPLES

Experimental Methods

Peptides and Materials

Colivelin (SEQ ID NO: 3) was synthesized as described in the document (Chiba T et al., J Neurosci (2005) 25: 10252-10261). Rabbit monoclonal anti-phospho-STAT3 antibody (Tyr705; 58E12) and rabbit monoclonal STAT3 antibody (79D7) was purchased from Cell Signaling Technology (Beverly, Mass.).

Animals and Treatments

Tg2576 mice were purchased from Taconic (Germantown, N.Y.). V642I-APP knockin mice were produced as described in the document (Kawasumi M et al., Eur J Neurosci (2004) 19: 2826-2838).

Behavioral Test

Y-maze test (YM) was performed as described in the document (Yamada M et al., Behav Brain Res (2005) 164: 139-146). The apparatus for YM is composed of three grey plastic arms (40 cm long, 12 cm high, 3 cm wide at the bottom, and 10 cm wide at the top). Mice were each allowed to explore the maze freely under observation for 8 minutes. Spontaneous alternation behavior % (SA %) is an indication of spatial working memory and is calculated using a ratio of the arm choices differing from the previous two choices to total choices during the run. Water-finding task (WFT) was performed as described in the document (Kawasumi M et al., Eur J Neurosci (2004) 19: 2826-2838). The testing apparatus consists of a grey plastic rectangular open field (50×30 cm, 10-cm-square grid line, and 15-cm-high walls) and a cubic alcove (10×10×10 cm) attached to one side of a longer wall. Mice were first allowed to explore freely for 3 minutes the apparatus (Training session) with a water tube provided within the alcove at 5 cm above the floor. After the Training session, mice were immediately deprived of water for 24 hours. Mice were then tested again in the same apparatus with water tube provided at 7 cm above the floor (Trial session). The time between the onset of exploration and entering to the alcove (Entering latency), initiation of drinking from the water tube (Drinking latency), and the number of grid-line crossing during the test were measured Elevated-plus maze (EPM) was performed as described in the document (Kawasumi M et al., Eur J Neurosci (2004) 19: 2826-2838). The testing apparatus set at 100 cm above the floor was made of four orthogonally crossed arms. Two arms were open while two arms were closed (a 50 cm×10 cm grey plastic floor plate with 10-cm-high grey walls). Mice were individually placed at the end of the open arm and allowed to explore the maze freely for 90 seconds. Examined three parameters were: (i) transfer latency (the time elapsed until the first entry to the closed arms); (ii) $1^{st}$ stay (the time from $1^{st}$ entry to the closed arms to $1^{st}$ escape from the arms); and (iii) cumulative time spent in open arms.

Immunohistochemistry

Immunohistochemical analysis was performed as described in the document (Yamada M et al., Behav Brain Res (2005) 164: 139-146; Chiba T et al., J Neurosci (2005) 25: 10252-10261). Mice were transcardially perfused with phosphate buffered saline (PBS) and then perfused with 4% paraformaldehyde (PFA). Paraffine-embedded sections or fresh frozen sections, each having a thickness of 10 µm, were prepared. Immunohistochemical detection was performed with anti-phospho-STAT3 antibody (1:100 dilution). Staining images were visualized with the ABC method (Vectastain Elite Kit, Vector, Calif. U.S.A.) or Tyramide signal enhancer kit (Perkin-Elmer).

Culture of Cells and Analysis of Phosphorylation

PC12 cells were cultured in DNEM (Wako) containing 10% serum (10%-DMEM). For phosphorylation analysis, PC12 cells (cultured at $1.6 \times 10^5$ cells/well in a 6-well plate containing serum-free DMEM for 24 hours) were stimulated with a ciliary neurotrophic factor (CNTF, 50 ng/ml), interleukin-6 (IL-6, 50 ng/ml), HN (10 µl, D-Ser14-HN (D-14, 10 µM, and Colivelin (100 pM) for 15 minutes. Cells were rinsed once with PBS and then lysed in a buffer solution containing phosphatase inhibitors (50 mM Tris HCl [pH7.4], 150 mM NaCl, 1% Triton-X 100, protease inhibitors, 1 mM EDTA, and phosphatase inhibitor cocktails 1 and 2 [Sigma]). Collected samples were separated by normal SDS-PAGE and were then electrically blotted onto PVDF membranes. Detection was performed using an anti-phospho-STAT3 (1:500 dilution) antibody and horseradish peroxidase (HRP)-labeled anti-rabbit IgG antibody (BioRad Laboratories, Hercules, Calif., U.S.A.). Immunoreactive bands were visualized using ECL Western Blotting Detection Reagents (Amersham Bioscience, Uppsala, Sweden). Immunoreactive bands corresponding to total-STAT3 antibody (1:3000 dilution) were subjected to detection on the identical membrane stripped and then determined to be controls.

Results

Age-Dependent STAT3 Inactivation in Alzheimer's Disease Model Mice

To examine the relationship between a STAT3 activation level and the onset of Alzheimer's disease, Alzheimer's model mouse brain sections were immunohistologically stained with an anti-phospho-STAT3 antibody (FIG. 1). We first compared amyloid precursor protein (APP) transgenic mice (Tg mice) Tg2576 having Swedish type mutant with their wild-type control littermates (Hsiao K et al., Science (1996) 274(5284): 99-102) (FIGS. 1 H-J). Phospho-STAT3 immunostaining revealed the loss of reactivity in Tg2576 mice at all stages (3, 12, and 18 months of age) compared with the wild-type control littermates (FIGS. 1E-J). Behavioral abnormality is detected in Tg2576 as early as 3 months of age, while no senile plaque formation is observed (King D L and Arendash G W, Physiol Behav (2002); 75(5): 627-42). It was suggested that STAT3 inactivation correlates with behavioral abnormality. To confirm the result, another type of model mice, V642I-APP knockin mice were used. V642I-APP knockin mice show only behavioral abnormality at 27 months of age without any detectable pathological abnormality (Kawasumi M et al., Eur J Neurosci (2004) 19: 2826-2838). We observed no differences between knockin mice and wild-type mice at 6 months of age (FIGS. 1A and 1C), while they confirmed the loss of phospho-STAT3 immunoreactivity in knockin mice at 28 months of age compared with wild-type mice (FIGS. 1B and D). At this time, when only the wild-type mice were observed, compared with 6-month-old mice, 28-month-old wild-type mice showed STAT3 inactivation, suggesting age-dependent STAT3 inactivation (FIGS. 1A and B).

STAT3 Inactivation in Alzheimer's Disease Patients' Brains

Next, we performed phospho-STAT3 immunostaining using the brain sections of both clinically and histopathologically diagnosed Alzheimer's disease patients and normal healthy patients (FIGS. 2A-H). We observed the significant loss of phospho-STAT3 immunoreactivity in the hippocampus of Alzheimer's disease patients, compared with the normal healthy brains of the healthy patients.

STAT3 Activation Via Colivelin Treatment Ameliorates Cognitive Dysfunction

Figure 3:
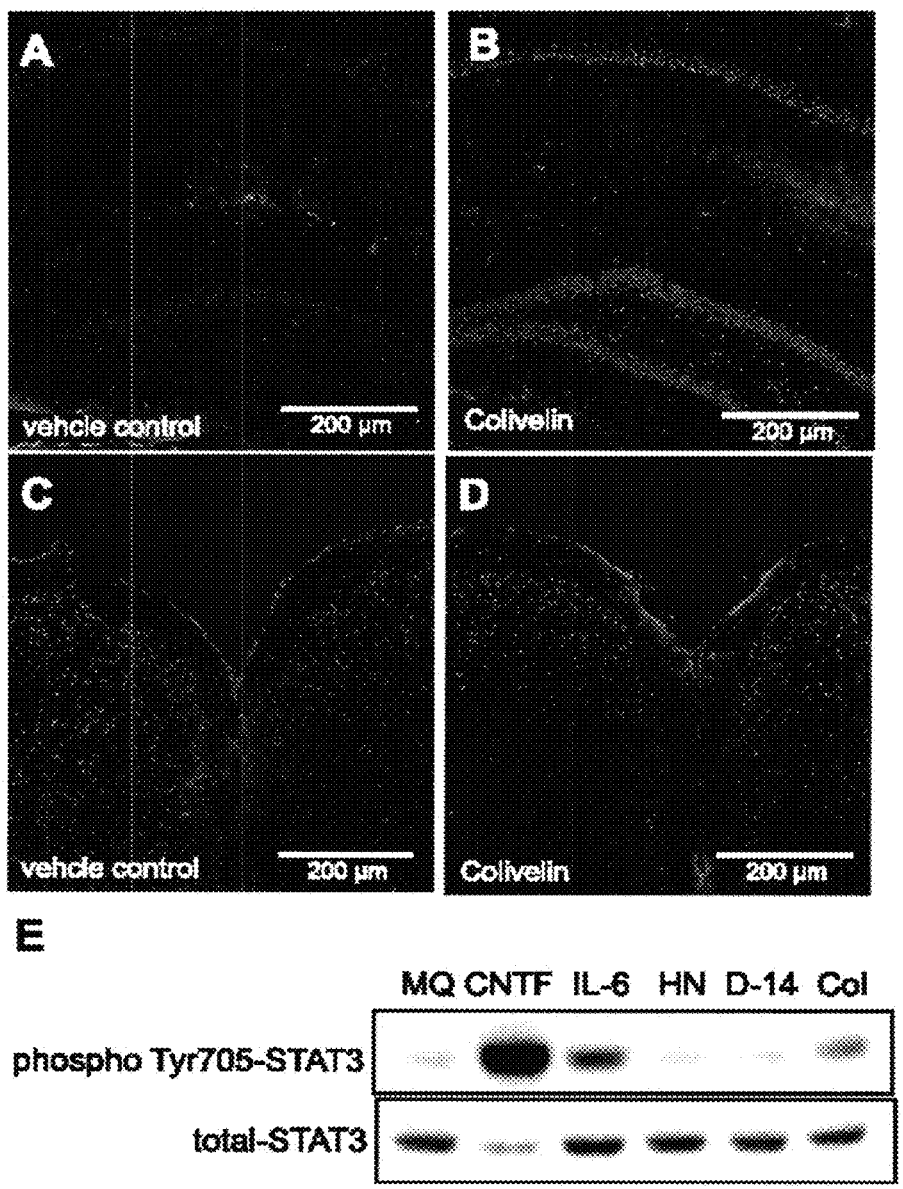
FIG. 3 shows the phosphorylation of STAT3 by Colivelin. To examine the ability of Colivelin to phosphorylate STAT3 in vivo, a solvent (FIGS. 3A and 3C) or Colivelin (FIGS. 3B and 3D) was administered transnasally to mice twice at 24 hours-intervals. Brain samples were collected 30 minutes after the final administration, and then fresh frozen sections were prepared therefrom. The sections were then stained with an anti-phospho-STAT3 antibody. Significant STAT3 phosphorylation was observed in the hippocampus of mice to which Colivelin had been administered (FIGS. 3A and 3B). However at this time in cerebral cortex (FIGS. 3C and 3D), no significant changes were observed. To examine the effect of Colivelin to phosphorylate STAT3 in vitro, PC12 cells were treated with a vehicle (MQ), CNTF, IL-6, Humanin (HN), D-Ser14-HN (D-14), and Colivelin (Col) for 24 hours for stimulation. Phosphorylated STAT3 and total STAT3 were detected by an immunoblot method (FIG. 3E). As a result, it was confirmed under the conditions that STAT3 had been phosphorylated by CNTF, IL-6, and Colivelin.
Figure 4:
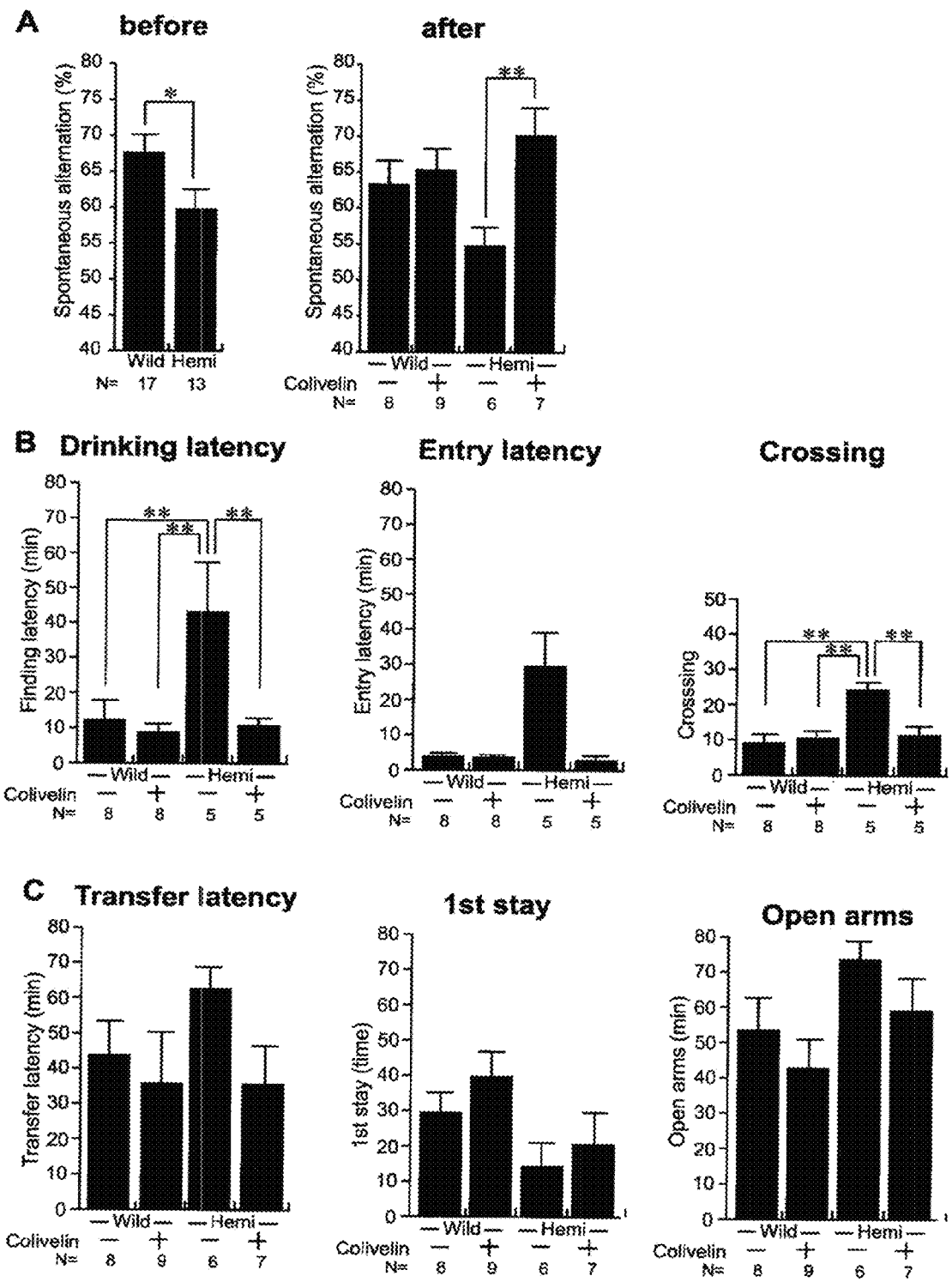
FIG. 4 shows the results of behavioral analysis of Tg2576 mice that have been subjected to Colivelin administration. Tg2576 mice and wild-type control mice at 15 months of age were tested by Y-maze test (YM) (FIG. 4A, left). Significant decreases were observed in SA % that is an indication of spatial working memory. Mice were then subjected to nasal administration of Colivelin or a vehicle for 3 weeks. Subsequently, mice were again tested by Y-maze test. It was revealed that SA % was significantly improved in Tg2576 to which Colivelin had been administered (FIG. 4A, right). Also in Tg2576 tested by water-finding task (WFT) (FIG. 4B), significant amelioration was observed concerning indices of memory including drinking latency, entering latency, and crossing. No significant differences were observed as a result of the elevated-plus maze (EPM) (FIG. 4C) test. However, Colivelin administration seemed to ameliorate tendencies observed in Tg2576 to which the vehicle had been administered, such as delay in transfer latency, shortened 1 stay, and prolonged time spent in open arm (difficult to fear).
Figure 5:
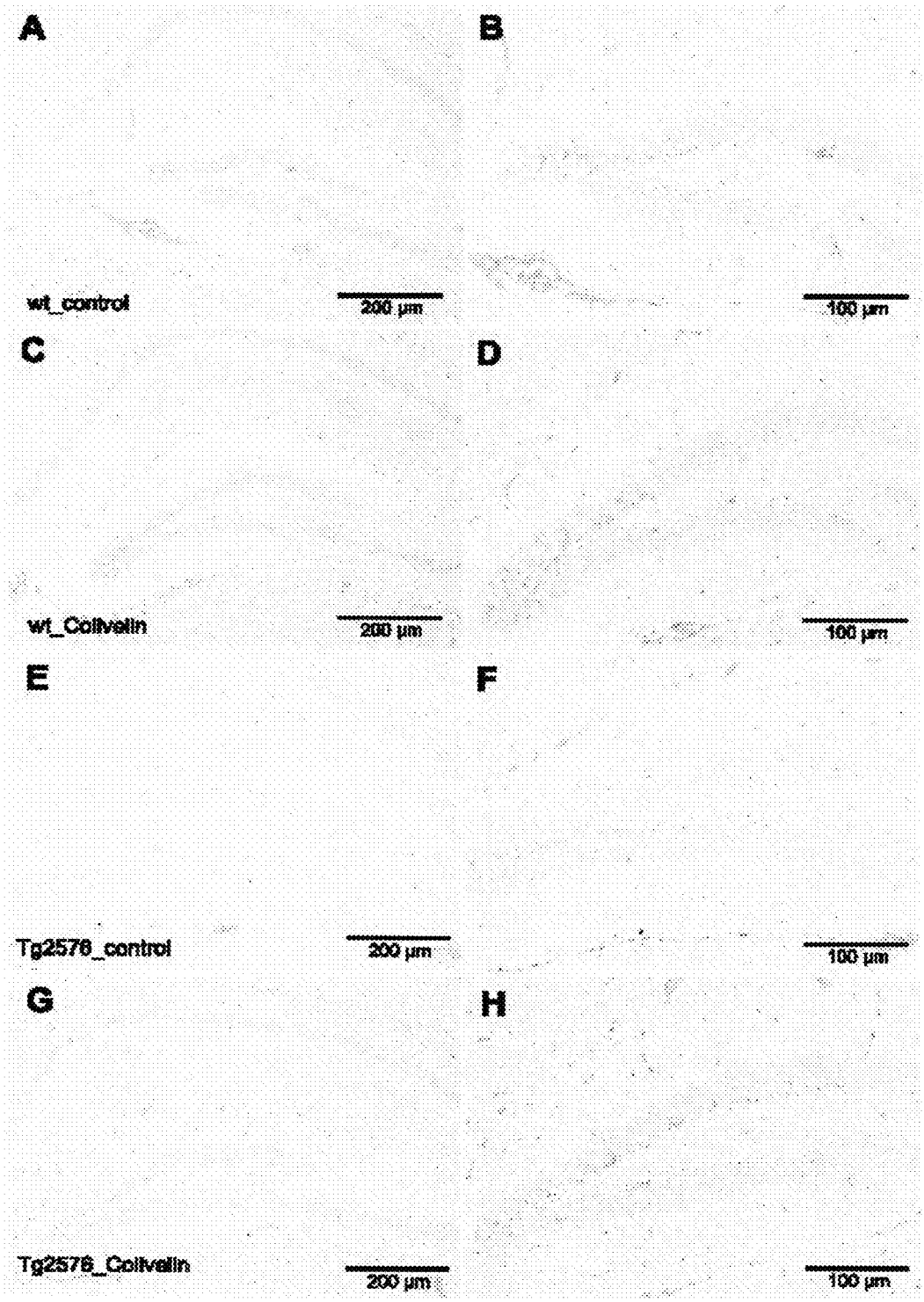
FIG. 5 shows the results of histological analysis of Tg2576 mice to which Colivelin had been administered. The brain sections of Tg2576 mice to which Colivelin had been administered were collected, paraffin-embedded samples were prepared therefrom, and then anti-phospho-STAT3 staining was performed.

It has been reported that Colivelin activates in vitro STAT3 so as to suppress cell death (Hashimoto Y et al., Life Sci (2005) 77: 3092-3104; Chiba T et al., J Neurosci (2005) 25: 10252-10261). We confirmed STAT3 activation in the brains of mice to which Colivelin had been nasally administered twice every 24 hours (FIGS. 3A-D). Hippocampus-predominant STAT3 phosphorylation (staining images of STAT3) was confirmed in the group of mice to which Colivelin had been administered compared with the control group of mice to which a vehicle had been administered (FIGS. 3A and B). However, at this time, no significant differences were confirmed in cerebral cortex between the two groups (FIGS. 3C and D). We also confirmed STAT3 phosphorylation in an in vitro experiment using PC12 cells. As a result, it was confirmed that STAT3 is phosphorylated by a ciliary neurotrophic factor (CNTF), IL-6, and Colivelin (Stephanou A and Latchman D S Growth Factors (2005) 23(3): 177-82) (FIG. 3E). To confirm the therapeutic effect of STAT3 activation, an experiment (nasal administration of Colivelin to mice) was conducted for Tg2576 mice, which had been tested by Y-maze test (YM) and confirmed to have memory disorder at 15 months of age (FIG. 4A, left panel). After 3 weeks of administration (administered every other day), their cognitive functions were analyzed by YM, water-finding task (WFT), and elevated-plus maze (EPM). As a result, improvement in cognitive functions was confirmed in both YM (FIG. 4A, right panel) and WFT (FIG. 4B). As a result of EPM, no significant changes were observed, however, the mice of the group to which Colivelin had been administered showed behavioral patterns similar to those observed in wild-type mice (FIG. 4C). We performed phospho-STAT3 immunostaining using the brains of these mice (FIG. 5). We observed significant loss of phospho-STAT3 immunoreactivity in the control Tg2576 mice to which the vehicle had been administered, compared with the wild-type mice. However, we confirmed recovery of phospho-STAT3 immunoreactivity in Tg2576 mice to which Coliverlin had been administered, suggesting that Colivelin administration activates again STAT3 that had been inactivated, so as to improve memory.

INDUSTRIAL APPLICABILITY

The present invention is useful for treatment and diagnosis of Alzheimer's disease or memory and/or cognitive disorders, and can be particularly expected in pharmaceutical applicability.

What is claimed is:

1. A method for screening for a therapeutic agent for human Alzheimer's disease or memory and/or cognitive disorders comprising,
   (a) providing a mouse model for Alzheimer's disease, administering a candidate drug to the mouse, obtaining a sample of hippocampal brain tissue from the mouse, and
   detecting, in vitro, activation of STAT3 in the hippocampal brain tissue sample, wherein when STAT3 is activated a phosphorylated STAT3 protein is detected in hippocampal brain tissue sample of the mouse compared with hippocampal brain tissue sample of a control mouse; or
   (b) providing a brain hippocampus-derived primary neuronal cell, which is derived from a human with Alzheimer's disease or a mouse or rat model for Alzheimer's disease,
   culturing the primary neuronal cell in the presence of a candidate drug, and
   detecting activation of STAT3 in the cultured cells, wherein the activation of STAT3 protein is correlated with an increase in phosphorylated STAT3 protein in total STAT3 protein detected in cultured primary neuronal cells when compared with control cells; and
   selecting the candidate drug associated with activation of STAT3 in the mouse and/or the cultured primary cultured neuronal cells for testing in a human having Alzheimer's disease, a memory disorder, and/or a cognitive disorder to determine if the candidate drug has a therapeutic effect toward Alzheimer's disease, the memory disorder, and/or the cognitive disorder.

2. The method according to claim 1, comprising measuring the degree of STAT3 protein activation in the hippocampal brain tissue sample from the mouse model, or in the cultured primary neuronal cells.

3. The method according to claim 2, wherein measurement is performed using an antibody specific to a phosphorylated STAT3 protein.

4. The method according to claim 3, wherein the antibody is labeled.

5. The method according to claim 1, wherein the STAT3 protein is a protein comprising the amino acid sequence of SEQ ID NO: 2.

6. The method according to claim 1, wherein the candidate drug is a small organic molecule, a peptide, a polypeptide, a protein, or a chemically modified derivative thereof.

7. The method according to claim 1, which comprises said step (a).

8. The method according to claim 1, which comprises said step (b).

9. A method for screening for a therapeutic agent for human Alzheimer's disease or memory and/or cognitive disorders comprising:
   (a) providing a mouse model for Alzheimer's disease, wherein the mouse model is a V642I-APP knockin mouse;
   (b) administering a candidate drug to the mouse;
   (c) obtaining a sample of hippocampal brain tissue from the mouse,
   (d) detecting, in vitro, activation of STAT3 in the mouse, wherein when STAT3 is activated a phosphorylated STAT3 protein is detected in hippocampal brain tissue of the mouse compared with a control mouse; and
   (e) selecting the candidate drug associated with activation of STAT3 in the mouse for testing in a human having Alzheimer's disease, a memory disorder, and/or a cognitive disorder to determine if the candidate drug has a therapeutic effect toward Alzheimer's disease, the memory disorder, and/or the cognitive disorder.

10. A method for screening for a therapeutic agent for human Alzheimer's disease or memory and/or cognitive disorders comprising:

(a) providing a mouse model for Alzheimer's disease, administering a candidate drug to the mouse,
  obtaining a sample of hippocampal brain tissue from the mouse, and
  detecting, in vitro, activation of STAT3 in hippocampal brain tissue sample,
wherein when STAT3 is activated a phosphorylated STAT3 protein is detected in hippocampal brain tissue sample of the mouse compared with hippocampal brain tissue sample of a control mouse; or (b) providing a brain hippocampus-derived primary neuronal cell, which is derived from a human with Alzheimer's disease or a mouse or rat model for Alzheimer's disease,
  culturing the primary neuronal cell in the presence of a candidate drug, and
  detecting activation of STAT3 in the cultured cells, wherein the activation of STAT3 protein is correlated with an increase in phosphorylated STAT3 protein in total STAT3 protein detected in the cultured primary neuronal cells when compared with control cells;

selecting the candidate drug associated with activation of STAT3 in the mouse and/or the cultured primary neuronal cells for testing in a human having Alzheimer's disease, a memory disorder, and/or a cognitive disorder to determine if the candidate drug has a therapeutic effect toward Alzheimer's disease, the memory disorder, and/or the cognitive disorder, wherein the candidate drug is a polypeptide comprising SEQ ID NO: 4: Ser Ala Leu Leu Arg Ser Ile Pro Ala Pro Xaa Xaa Xaa Xaa Leu Thr Xaa Xaa Pro wherein Xaa at position 11 is $Xn_1$ consisting of an amino acid sequence (Arg or Ala)-(Gly or Ala)-(Phe or Ala)-(Ser or Ala), Xaa at position 12 is Cys, Arg, Lys, or His, Xaa at position 13 is Leu or Arg, Xaa at position 14 is $Xn_2$ consisting of an amino acid sequence (Leu or Ala)-(Leu or Ala), and Xaa at position 17 is (Gly, L-Ser, or D-Ser), Xaa at position 18 is $Xn_3$ consisting of an amino acid sequence comprising (Glu or Ala)-(Ile or Ala)-(Asp or Ala)-(Leu or Ala).

\* \* \* \* \*